(12) United States Patent
Choudhary et al.

(10) Patent No.: US 6,548,722 B1
(45) Date of Patent: Apr. 15, 2003

(54) PROCESS FOR THE PREPARATION OF SUBSTITUTED AROMATIC COMPOUND EMPLOYING FRIEDEL-CRAFTS REACTION USING A REUSABLE BASIC ANIONIC CLAY CATALYST

(75) Inventors: Vasant Ramchandra Choudhary, Maharashtra (IN); Suman Kumar Jana, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/685,682

(22) Filed: Oct. 10, 2000

(51) Int. Cl.$^7$ ............................................. C07C 309/00
(52) U.S. Cl. ...................... 585/467; 568/332; 568/628; 568/734; 568/928
(58) Field of Search ................................ 568/309, 319, 568/322, 323, 332, 628, 734, 928; 585/446, 452, 453, 467, 468

(56) References Cited

U.S. PATENT DOCUMENTS

| | | | |
|---|---|---|---|
| 3,678,122 A | 7/1972 | Schmerling | |
| 3,679,760 A | 7/1972 | Schmerling | |
| 3,833,672 A | 9/1974 | Debat | |
| 4,049,733 A | 9/1977 | Martan | |
| 4,379,092 A | 4/1983 | Devic | |
| 4,929,784 A | 5/1990 | Klinkmann et al. | |
| 5,068,481 A | 11/1991 | Akatsu et al. | |
| 5,072,017 A | 12/1991 | Buysch et al. | |
| 5,258,554 A | 11/1993 | Langer et al. | |
| 6,180,557 B1 * | 1/2001 | Choudhary et al. | 502/204 |
| 6,215,035 B1 * | 4/2001 | Choudhary et al. | 585/467 |

FOREIGN PATENT DOCUMENTS

| | | | |
|---|---|---|---|
| DE | 2451037 | | 4/1976 |
| DE | 2456747 | | 6/1976 |
| DE | 2547030 | | 5/1977 |
| DE | 4038933 | | 6/1992 |
| EP | 0352878 | * | 1/1990 |
| FR | 2667063 | | 3/1992 |
| JP | 48099154 | | 12/1973 |
| JP | 59186937 | | 10/1984 |
| SU | 394353 | | 8/1973 |

* cited by examiner

*Primary Examiner*—Sreeni Padmanabhan
(74) *Attorney, Agent, or Firm*—Dority & Manning, P.A.

(57) ABSTRACT

A process for Friedel-Crafts type liquid-phase alkylation or acylation of an aromatic compound using a hydrotalcite-type basic anionic clay catalyst represented by a formula:

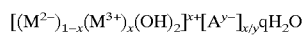

where
$M^{2+}$ is a divalent cation selected from $Mg^{2+}$, $Zn^{2+}$, $Ni^{2+}$, $Co^{2+}$, $Mn^{2+}$, $Cu^{2+}$ or a mixture thereof;
$M^{3+}$ is a trivalent cation selected from $Ga^{3+}$, $In^{3+}$ $Al^{3+}$, $Fe^{3+}$ $Cr^{3+}$ or a mixture thereof; x is a mole fraction of trivalent cations in the range of about 0.05 to about 0.5; 0 is oxygen; H is hydrogen; $A^{y-}$ is an anion; y minus is an anionic negative charge having a value of 1 minus or 2 minus; and q is a number of water molecules, as the water of hydration; and involving following steps:

i. pretreating said catalyst by contacting it with a halogen containing compound in the presence or absence of a non-aqueous solvent and optionally washing the pretreated catalyst with non-aqueous solvent or liquid aromatic compound to be alkylated or acylated; and then ii. contacting a liquid reaction mixture comprising said aromatic compound and said alkylating or acylating agent in the presence or absence of a non-aqueous solvent with the catalyst obtained from step (i) in a stirred batch reactor fitted with a reflux condenser under vigorous stirring, in the presence or absence of an inert gas bubbling through the reaction mixture, at effective reaction conditions;

iii. cooling the reaction mixture to a temperature about 30° C., removing said catalyst from the reaction mixture by filtration and then separating the reaction products from the reaction mixture, and optionally washing the used catalyst by non-aqueous solvent, and if desired, iv. reusing the used catalyst directly with or without drying for the subsequent reaction batch avoiding step (i), is disclosed.

18 Claims, No Drawings

PROCESS FOR THE PREPARATION OF SUBSTITUTED AROMATIC COMPOUND EMPLOYING FRIEDEL-CRAFTS REACTION USING A REUSABLE BASIC ANIONIC CLAY CATALYST

FIELD OF THE INVENTION

A process for the preparation of substituted aromatic compounds employing Friedel-Crafts reaction and using a basic anionic clay hydrotalcite-type solid catalyst. This invention particularly relates to a process for the alkylation or acylation of aromatic compounds by an alkylating or acylating agent for preparing alkylated or acylated aromatic compounds, using basic anionic clay hydrotalcite-type solid catalyst.

BACKGROUND AND PRIOR ART REFERENCES

The process for this invention could be used for the preparation of alkylated or acylated aromatic compounds, which are fine chemicals and/or used as intermediates in the preparation of fine chemicals or specialty chemicals in dyes and pharmaceutical industries and other chemical industries.

Both the homogeneous and heterogeneous catalyzed liquid phase Friedel-Crafts processes for the preparation of alkylated and acylated aromatic compounds are known in the prior art.

Friedel-Crafts Type Reactions Catalysed by Homogeneous Acid Catalysts

The Friedel-Crafts type reactions, such as alkylation and acylation of aromatic compounds by various alkylating or acylating agents, using homogeneous Lewis acid catalysts, such as $AlCl_3$, $BF_3$, $ZnCl_2$ and other metal chlorides and protonic acid catalysts, such as $H_2SO_4$, $H_3PO_4$, HF, etc., are well known in the prior art [ref. G. A. Olah, in Friedel-Crafts and related reactions: vol. Ill, Acylation and related reactions, Wiley-Interscience Publ., New York, 1964].

A use of $CuCl_2$ as a homogeneous catalyst in the benzylation of benzene or substituted benzenes by benzyl chloride is disclosed in two US patents: U.S. Pat. No. 3,678,122 (1972) and U.S. Pat. No. 3,679,760(1972). A French patent, FR 2,144,578(1973), disclosed benzylation of p-substituted phenols by benzyl halides in the presence of homogeneous $ZnCl_2$ catalyst. A USSR patent, U.S. Ser. No. 394,353 (1973), disclosed a use of $SnSO_4$ or $SnCl_2$ as homogeneous catalyst for the benzylation with benzyl chloride of m-dimethoxy benzene. A Japanese patent, JP 7399,154 (1973), disclosed preparation of dibenzyl benzene derivatives by benzylation of benzene or substituted benzenes using $AlC_3$, $FeCl_3$ and 98% $H_2SO_4$. A use of $H_2SO_4$ or $H_3PO_4$ and optionally 4-$CH_3C_6H_4SO_3H$, $ZnCl_2$, $BF_3$, ect. in the preparation of o-benzyltoluenes by the reaction of α o-chloromethyltoluene with a benzene derivative is disclosed in a German patent, Ger. Offen 2,456,747 (1976). A use of phosphoric acid and optionally $H_2SO_4$ or a Friedel-Crafts type metal halide in the benzylation of benzene with benzylether is disclosed in a US Patent, U.S. Pat. No. 4,049,733 (1977).

A German patent, Ger. offen 2,451,037 (1976), disclosed the use of HF as a catalyst for the benzoylation of aromatic compounds.

A French patent, FR 2,496,097 (1982) disclosed the acylation of benzene by phthalic anhydride using HF—$BF_3$ mixture.

More recently, an European Patent, EP 53.8,704 (1993), disclosed a process for the preparation of p-substituted o-benzylphenols by treating phenols, p—R $C_6H_4OH$ (R=halo, alkyl, OH, alkoxy, alkylmercapto, aryl, aryloxy or arylmercapto), with $ArCH_2X$ (Ar=corresponding aryl nucleus; X=halo, arylcarboxy, phenylsulfatoxy, hydroxy, alkoxy etc.) in a continuously functioning distillation apparatus in the presence of dissolved acid catalyst.

The main disadvantages of the Friedel-Crafts processes based on the use of homogeneous acid catalyst are as follows:

1) The separation and recovery of the dissolved acid catalysts from the liquid reaction mixture is difficult.
2) The disposal of the used acid catalysts creates environmental pollution.
3) The homogeneous acid catalysts also pose several other problems such as high toxicity, corrosion, spent acid disposal and use of more than the stoichiometric amount.

Friedel-Crafts Type Reactions Catalysed by Heterogeneous Solid Acid Catalysts A German patent, Ger.Offen 2,547,030 (1977), disclosed the preparation of o-benzyl toluenes by the reaction of o-methylbenzyl halides with substituted benzenes in the presence of Al-silicate. The 2-$CH_3C_6H_4CH_2Cl$ was stirred with toluene and Al-silicate (25% $Al_2O_3$) at 110° C. to give 81% 2-methylbenzyltoluene. According to a Japanese patent, JP 59,186,937 (1984), o-benzylphenol was prepared by the liquid phase reaction of benzyl alcohol with phenol in the presence of $\gamma$-$Al_2O_3$. For example 7.5 g $\gamma$-$Al_2O_3$ was added to a mixture of 32.5 g benzyl alcohol and 47 g phenol at 190° C. under stirring to give a product-containing 49.9% o-benzylphenol. A German Patent, Ger. Offen DE 3,700,917 (1988), disclosed the preparation of p-substituted o-benzylphenols by alkylation of p-substituted phenols with benzylalcohol in the presence of Na—Y type zeolite. A mixture of 0.5 mole 4-$ClC_6H_4OH$, 0.1 mole $C_6H_5CH_2OH$ and 0.6 g of Na—Y type zeolite was heated at 200° C. for 3 hrs to give 25.4% 2-benzyl-4-chlorophenol.

A French patent, FR 2,667,063 (1992), disclosed the preparation of 4-substituted benzophenones by acylation of substituted benzenes by substituted benzoic acid in the presence of H$\gamma$-and H$\beta$ type zeolites. Accordingly, 4-$ClC_6H_4COOH$ and PhMe were heated 4 h at 200° C. under $2 \times 10^5$ Pa in the presence of calcined zeolite H$\beta$ to give 84.4% 4-(4-Cl $C_6H_4$ CO)$C_6H_4$ Me.

A recent paper by Vincent et al. (ref. Tetrahedron Lett. 35, 1994, 2601), disclosed that H-ZSM-5 zeolite can catalyze the acylation by benzoyl chloride of phenol and anisole but not the acylation with benzoyl chloride of benzene, halobenzene and naphthalene, at 120° C. for 5 h.

A German patent, Ger. Offen DE 3,836,780 (1990), disclosed the process for the preparation of benzylbenzenes from benzenes and benzyl alcohols in the presence of activated bleaching earth and a diluent at 90–140° C. According to Japanese patent, fP 03,170,442 (1991), benzylbiphenyls are manufactured by alkylating biphenyl and diphenylmethane with ≧1 compound from benzyl halides, benzyl alcohol, benzyl ether in the presence of a zeolite or silica-alumina catalyst. An European patent, EP 428,081 (1991), disclosed a process of alkylation of alkylbenzenes with benzyl chloride in the presence of H—Y or H—L zeolite catalyst. A German patent, Ger. Offen DE 4,038,933 (1992), disclosed a process for alkylation of aromatics using technical carbon catalysts.

Alkylation or acylation of aromatic compound involves electrophilic substitution of H from the aromatic nucleus of the aromatic compound. It is well known in the prior art that the electrophilic substitution is favored by the presence of electron donating groups, such as OH, alkyl, alkoxy, phenoxy, amine, alkyl amine, SH, etc., in the aromatic compound. Whereas the electrophilic substitution is inhibited by the presence of electron withdrawing groups such as halo, nitro, cyano, carboxy, aldehyde, etc., in the aromatic compound [ref. G.A.Olah, in Friedel-Crafts and related reactions, Wiley-Interscience Publ, New York, 1963].

Although some limitations of the homogeneous acid catalyzed processes are overcome in the prior art of heterogeneous solid catalyzed processes described above, the alkylating or acylating activity of the solid acid catalysts used in the prior art processes is low, particularly when no electron donating group is present in the aromatic compound, such as benzene, naphthalene and anthracene, to be alkylated or acylated. Both the homogeneous and heterogeneous acid catalysts of the prior art are highly moisture sensitive, and hence demand moisture-free or thoroughly dried reactants, solvents and catalyst for the Friedel-Crafis processes. In presence of moisture in the reaction mixture, both the above homogeneous and heterogeneous catalysts show poor activity in the Friedel-Crafts type processes. Hence there is a great practical need for finding more efficient and also moisture insensitive solid catalyst for the alkylation or acylation of aromatic compounds. There is also a need for finding highly efficient non-acidic or basic solid catalyst for alkylating or acylating aromatic compounds, which are ad sensitive.

This invention is made with the following objects so that most of the drawbacks or limitations of the prior art homogeneous and heterogeneous catalyzed processes for the Friedel-Crafis type alkylation or acylation reactions could be overcome.

OBJECTS OF THE INVENTION

The main object of this invention is to provide a liquid phase process for the alkylation or acylation of aromatic compounds, including those not containing electron donating groups, using a basic anionic clay hydrotalcite-type catalyst, which has high activity not only when the aromatic ring activating groups (i.e. electron donating groups such as alkyl, alkoxy, hydroxy, phenoxy, etc) are present in the aromatic ring to be alkylated or acylated but also when the ring activating group in the aromatic ring to be alkylated or acylated is absent, so that the reaction temperature is low and/or time for completing the reaction is short.

Other important object of this invention is to provide a liquid phase process for the alkylation or acylation of aromatic compounds, using a basic anionic clay hydrotalcite-type solid catalyst which is easily separable and reusable in the process for several times.

Another important object of this invention is to provide a solid catalyzed liquid phase process for the alkylation or acylation of aromatic compounds even in the presence of moisture in the reaction mixture.

SUMMARY OF THE INVENTION

A process for Friedel-Crafis type liquid-phase alkylation or acylation of an aromatic compound using a hydrotalcite-type basic anionic clay catalyst represented by a formula:

where $M^{2+}$ is a divalent cation selected from $Mg^{2+}$, $Zn^{2+}$, $Ni^{2+}$, $Co^{2+}$, $Mn^{2+}$, $Cu^{2+}$ or a mixture thereof, $M^{3+}$ is a trivalent cation selected from $Ga^{3+}$, $In^{3+}$, $Al^{3+}$, $Fe^{3+}$, $Cr^{3+}$ or a mixture thereof; x is a mole fraction of trivalent cations in the range of hydrogen; $A^{y-}$ is an anion; y minus is an anionic negative charge having a value of 1 minus or 2 minus; and q is a number of water molecules, as the water of hydration, said process comprising the following steps:

i. pretreating said catalyst by contacting it with a halogen containing compound in the presence or absence of a non-aqueous solvent and optionally washing the pretreated catalyst with non-aqueous solvent or liquid aromatic compound to be alkylated or acylated; and then ii. contacting a liquid reaction mixture comprising said aromatic compound and said alkylating or acylating agent in the presence or absence of a non-aqueous solvent with the catalyst obtained from step (i) in a stirred batch reactor fitted with a reflux condenser under vigorous stirring, in the presence or absence of an inert gas bubbling through the reaction mixture, at effective reaction conditions;

iii. cooling the reaction mixture to a temperature about 30° C., removing said catalyst from the reaction mixture by filtration and then separating the reaction products from the reaction mixture, and optionally washing the used catalyst by non-aqueous solvent; and if desired, iv. reusing the used catalyst directly with or without drying for the subsequent reaction batch avoiding step (i), is disclosed.

DETAILED DESCRIPTION OF THE INVENTION

Accordingly, this invention provides a process for the preparation of substituted aromatic compound represented by a formula

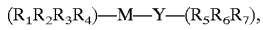

from substituted aromatic compound having formula:

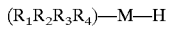

with an alkylating or acylating agent represented by a formula:

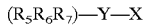

to produce corresponding alkylated or acylated aromatic compound represented by a formula:

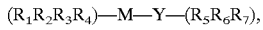

wherein, M is an aromatic nucleus such as single aromatic ring containing 6 C-atoms and 1 H-atom or fused two aromatic rings containing 10 C-atoms and 3 H-atoms or three fused aromatic rings containing 14 C-atoms and 5 H-atoms; $R_1$, $R_2$, $R_3$ and $R_4$ are groups attached to the aromatic nucleus, M; Y, which is a nucleus of alkylating or acylating agent, is selected from $C_6H_2$—$C_nH_{2n}$, $C_6H_2$—CO, $C_nH_{2n-2}$, $C_mH_{2m-4}$ and C—CO; $R_5$, $R_6$ and $R_7$ are group attached to the nucleus of alkylating or acylating agent, Y; X is a halogen or hydroxyl chemical group; H is hydrogen; C is carbon; O is oxygen; n and m are integer numbers having value above zero and above one, respectively; using a basic anionic clay catalyst represented by a formula:

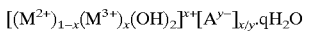

where $M^{2+}$ is a divalent cation selected from $Mg^{2+}$, $Zn^{2+}$, $Ni^{2+}$, $Co^{2+}$, $Mn^{2+}$, $Cu^{2+}$ or a mixture thereof; $M^{3+}$ is a trivalent cation selected from $Ga^{3+}$, $In^{3+}$, $Al^{3+}$, $Fe^{3+}$, $Cr^{3+}$ or a mixture thereof; x is a mole fraction of trivalent cations in the range of about 0.05 to about 0.5; 0 is oxygen; H is hydrogen; $A^{y-}$ is an anion; y minus is an anionic negative charge having a value of 1 minus or 2 minus; and q is a number of water molecules, as the water of hydration; and said catalyst having X-ray diffraction pattern similar to that of a typical hydrotalcite anionic clay material, with or without supporting it on a porous catalyst carrier;

the process comprises:

i. pretreating said catalyst by contacting it with a halogen containing compound in the presence or absence of a non-aqueous solvent and optionally washing the pretreated catalyst with non-aqueous solvent or liquid aromatic compound to be alkylated or acylated, and then ii. contacting a liquid reaction mixture comprising said aromatic compound and said alkylating or acylating agent in the presence or absence of a non-aqueous solvent with the catalyst obtained from step (i) in a stirred batch reactor fitted with a reflux condenser under vigorous stirring, in the presence or absence of an inert gas bubbling through the reaction mixture, at following reaction conditions: weight ratio of catalyst to alkylating or acylating agent in the range from about 0.01 to about 2.0, mole ratio of aromatic compound to alkylating or acylating agent in the range from about 0.1 to about 100, weight ratio of non-aqueous solvent to aromatic compound in the range from zero to about 100, reaction temperature in the range from about 10° C. to about 300° C., pressure in the range from about 0.5 atm to about 10 atm, gas hourly space velocity of inert gas bubbled through the liquid reaction mixture in the range from zero $h^{-1}$ to about 5000 $h^{-1}$ and reaction period in the range from about 0.02 h to about 100 h;

iii. cooling the reaction mixture to a temperature about 30° C., removing said catalyst from the reaction mixture by filtration and then separating the reaction products from the reaction mixture, and optionally washing the used catalyst by non-aqueous solvent; and iv. reusing the used catalyst directly with or without drying for the subsequent reaction batch avoiding step (i).

Each of $R_1$, $R_2$, $R_3$ and $R_4$ groups may be H or $C_nH_{2n+1}$ or $C_mH_{2n-1}$ or $C_6H_5$ or $C_nH_{2n}C_6H_5$ or OH or $OC_nH_{2n+1}$ or $OC_6H_5$ or halogen or $NO_2$ or $NH_2$ or $NHC_nH_{2n+1}$ or $N(C_nH_{2n+1})_2$ or $NHCOC_nH_{2n+1}$ or $NHCOC_6H_5$ or CN or CHO or COOH or $COOC_nH_{2n+1}$ or $COC_nH_{2n+1}$ or $SO_3H$ or $SO_3C_nH_{2n+1}$ or SH or alkyl mercapto group or aryl mercapto group and each of $R_5$, $R_6$ and $R_7$ chemical groups may be H or $CH_3$ or $C_2H_5$ or OH or $OCH_3$ or $OC_2H_5$ or $NO_2$ or halogen or $NH_2$, wherein n & m are integers greater than or equal to 1 and 2, respectively, and C,H,N,O and S are chemical elements—carbon, hydrogen, nitrogen, oxygen and sulfur, respectively.

The main finding of this invention is that, the said catalyst, which is basic in nature, shows high activity in the alkylation or acylation of aromatic compounds not only when the electron donating group, which is aromatic ring activating group, is present in the aromatic ring to be alkylated or acylated but also when the electron donating group is absent in the aromatic ring to be alkylated or acylated and hence the reaction temperature is low and/or the time required for completing the reactions is short.

Other important finding of this invention is that said solid catalyst can be separated easily and reused repeatedly in the process. Another important finding of this invention is that the alkylation or acylation of aromatic compound over said catalyst occurs with high reaction rates even in the presence of moisture in the reaction mixture containing aromatic compound to be alkylated or acylated, alkylating or acylating agent, solid catalyst and solvent, if used. Yet another important finding of this invention is that the pretreatment of the said catalyst with halogen containing compound in the step I of said process is essential for activating said catalyst.

Basic anionic clays Having hydrotalcite structure are well known in the prior art Methods of the preparation of hydrotalcite-type basic anonic clays are also known in the prior art [ref Cavani et al. Catalysis Today, vol. 11, page 173—301, (1991)].

In the said anionic clay catalyst, the anion, $A^{y-}$, may be mono or divalent anion, such as $(CO_3)^{2-}$, $(OH)^{1-}$, $(CH_3COO)^{1-}$, $(SO4)^{2-}$, $(HSO_4)^{1-}$, $(HCO_3)^{1-}$, $(NO_3)^{1-}$, $(ClO_4)^{1-}$, mono or divalent anion.

In the process of this invention, the pretreatment to said anionic clay catalyst may be effected by contacting it with a liquid halo organic compound in the presence or absence of non-aqueous solvent above room temperature for a period sufficient to activate the catalyst. The pretreatment to the said catalyst may also be effected by contacting it with a halogen compound in gaseous or vapor form, such as HCl, HBr, HF, $Cl_2$, $Br_2$, $F_2$ or halo organic compound or a mixture thereof at or above room temperature for a period sufficient to activate the catalyst. The halo organic compound used in the catalyst pretreatment may be benzyl chloride or bromide, benzoyl chloride or bromide, acetyl chloride or bromide, halo hydrocarbons, other chloro, bromo and fluoro organic compounds or a mixture thereof In the process of the present invention, the preferred reaction temperature may be between 20° C. and 200° C.; the preferred reaction pressure may be between 1 atm and 5 atm; the preferred reaction period may be between 0.05 h and 20 h; the preferred gas hourly space velocity of inert gas bubbled through the reaction mixture may be between 50 $h^{-1}$ and 500 $h^{-1}$ the preferred \wt. ratio of catalyst to alkylating or acylating agent may be between 0.03 and 0.9; the preferred mole ratio of aromatic compound to alkylating or acylating agent may be between 1.0 and 20; the preferred wt. ratio of non-aqueous solvent to aromatic compound may be between zero and 20; each of the preferred $R_1$, $R_2$, $R_3$ and $R_4$ chemical groups may be selected from hydrogen (H), alkane $(C_nH_{2n+1})$, olefinic $(C_mH_{2m-1})$, phenyl $(C_6H_5)$, alkoxy $(OC_nH_{2n+1})$, phenoxy $(OC_6H_5)$, hydroxyl (OH), aldehydic (CHO), ketonic (RCO), amine $(NH_2)$, amide $(CONH_2)$, thio (SH) and sulfonic acid $(HSO_3)$ groups (wherein n and m are integers having value $\geq 1$ and $\geq 2$, respectively); each of the preferred $R_5$, $R_6$ and $R_7$ chemical groups may be selected from hydrogen, alkane, olefinic, phenyl, halogen (Cl or Br or I or F), nitro $(NO_2)$ and cyano (CN) groups; the preferred chemical group X may be selected from Cl, Br and OH; the preferred divalent cation of the said catalyst may be selected from $Mg^{2+}$ $Zn^{2+}$ or a mixture thereof; the preferred trivalent cation of the said catalyst may be selected from $Ga^{3+}$, $In^{3+}$, $Fe^{3+}$ or a mixture thereof; the preferred anion, $A^{y-}$, of the said catalyst may be selected from $(CO_3)^{2-}$, $(OH)^{-1}$ or a mixture thereof; the preferred mole fraction, x, of the trivalent cation of the said catalyst may be between 0.1 and 0.4; and the preferred halogen containing compound used for pretreating said catalyst in step (i) of the process may be selected from gaseous hydrogen halides, such as HCl and HBr, gaseous halogens, such as $C_2$ and $Br_2$ or from liquid halo organic compounds, such as benzyl chloride or bromide, benzoyl chloride or bromide, acetyl chloride or bromide, The process of this invention can be carried out in a stirred batch reactor, fitted with a reflux condenser and arrangement for bubbling inert gas through the reaction mixture, known in the prior art for carrying out liquid phase reactions.

In the process of this invention, the main products formed are said alkylated or acylated aromatic compound and a by-product HX, wherein H=hydrogen and X=halogen or OH, depending upon the alkylating or acylating agent used.

In the process of this invention, the reactants namely aromatic compound and alkylating or acylating agent are converted partially or completely to the corresponding products.

The process of this invention may be carried out with or without using solvent, such as ethylene dichloride, nitrobenzene, nitromethane, chlorobenzene, n-hexane, n-heptane, n-octane or any other solvents. In the process of this invention, the role of solvent, if used, is to dissolve solid reactant or reactants, to dilute reactants and/or to facilitate the reaction between aromatic compound and alkylating or acylating agent. However, solvent may not be used in the process of this invention when both the reactants are liquids at said reaction conditions. Normally, said solvent is not converted in the process of this invention.

In the process of this invention, the role of inert gas bubbling continuously through the reaction mixture is to remove continuously said by-product from the reaction mixture so that the reverse reaction is avoided or minimized and the time required for completing the reaction is shortened. In the absence of bubbled inert gas, the reaction can still take place but with incomplete conversion and/or requiring longer period.

In the process of this invention, the role of the reflux condenser fitted with the reactor is to condense reactants and solvent, if used, and to return them back to the reaction mixture and allow the inert gas, which is continuously bubbling through the reaction mixture, along with said by-product to escape from the reaction mixture.

In the process of this invention, the reaction pressure above atmospheric pressure may be used to allow the reaction to be carried out at temperature higher than the normal boiling point of the reactants and/or solvent, by increasing the boiling point of said reactants and/or solvent with increasing the reaction pressure.

Said catalyst, used in the process of this invention, is heterogeneous with respect to the reaction mixture and can be removed from the reaction mixture simply by filtration and the removed catalyst, after washing with solvent or said liquid aromatic compound, which is to be alkylated or acylated, can be reused in the said process.

Said pre-treatment to said catalyst in step (i) of the process of present invention is essential for activating the catalyst so that the catalyst shows its high activity for catalyzing the alkylation or acylation reaction. The catalyst in the process of this invention can be easily separated from the reaction mixture simply by filtration. The used catalyst of this process can be reused in the process several times. The reused catalyst shows high activity in the process of this invention.

The role of said catalyst is to activate both the reactants—aromatic compound and alkylating or acylating agent and thereby to increase rate of the reaction.

By the process of this invention, benzene (which does not contain any electron donating group) can be benzylated with benzyl chloride to diphenyl methane with 100% conversion of benzyl chloride, at a temperature of 80° C. for a reaction period of 0.1 h and benzene can also be benzoylated with benzoyl chloride to benzophenone with 90% conversion of benzoyl chloride for a reaction period of 3 h.

The present invention is described with respect to the following examples illustrating the process of this invention for the alkylation or acylation of aromatic compounds using solid basic anionic clay catalyst, having hydrotalcite structure. These examples are provided for illustrative purposes only and are not to be construed as limitations on the process of this invention.

DEFINITION OF TERMS USED IN THE EXAMPLES

Conversion of reactant (%)=mole % of the reactant converted to all products. All the ratios of aromatic compounds to alkylating or acylating agent are mole ratios. All the solid catalyst to alkylating or acylating agent and solvent to aromatic compound ratios are weight ratios.

The flow rates of gases are measured at 0° C. and 1 atm pressure. Gas hourly space velocity (GHSV) is volume of gas, measured at 0° C. and 1 atm pressure, passed through unit volume of the liquid reaction mixture per hour.

Ac and Aa represent aromatic compound to be alkylated or acylated and alkylating or acylating agent, respectively.

Example-1

This example illustrates the process of this invention for the alkylation of benzene and toluene by benzyl chloride or benzyl bromide to the corresponding alkylated aromatic compounds, using a $[(Mg^{2+})_{0.75}(Ga^{3+})_{0.25}(OH)_2]^{0.25+}$ $[CO_3^{2-}]_{0.125} \cdot q \cdot H_2O$ catalyst.

The above catalyst was prepared as follows: First an aqueous solution containing 6.83 g (26.7 mmol) $Ga(NO_3)_3 \cdot xH_2O$ and 20.48 g (79.9 mmol) $Mg(NO_3)_2 \cdot 6H_2O$ in 100 cm$^3$ of water was prepared. 2.76 g (20 mmol) $K_2CO_3$ and 15.19 g (270.72 mmol) KOH in 300 cm$^3$ of water were dissolved to make a second solution. These two solutions were added dropwise into a flask containing 200 cm$^3$ of water at 313 K under vigorous stirring. The rate of addition of the two solutions was controlled in order to keep a constant pH of 11–12, which was monitored continuously throughout the co-precipitation procedure by means of a pH-meter. After completing the addition of the solutions, the white gel obtained was immediately washed with de-ionized water several times and separated in a centrifuige. After this, the white paste was dried in an oven in static air at 353 K for 24 h.

The XRD data of the white solid anionic clay produced was obtained using $CuK_{60}$ radiation, the XRD data, 2θ value and relative intensity of major XRD peaks, of the anionic clay are given below:

| 2θ (degree): | 11.0 | 22.2 | 34.0 |
|---|---|---|---|
| Relative intensity (%): | 100 | 54 | 29 |

The XRD data are similar to that of hydrotalcite [ref. Cavani et al. Catalysis Today, vol. 11, page 173–301, (1991)].

The catalytic alkylation reaction over the hydrotalcite-type anionic clay catalyst was carried out by I) first pre treating 0.1 g catalyst in a stirred batch reactor (capacity: 25 cm$^3$) with 1 g benzyl chloride dissolved in 13 ml toluene at 110° C. under reflux for a period of 2 h, and washing the pre-treated catalyst with the aromatic compound to be alkylated (benzene or toluene), II) contacting said pre-treated catalyst with 15 cm$^3$ liquid reaction mixture containing aromatic compound to be alkylated or acylated and alkylating or acylating agent with or without non-aqueous moisture-free solvent, in a stirred batch reactor (capacity: 25 cm$^3$) and fitted with a reflux condenser, mercury thermometer dipped in the reaction mixture and an inlet tube for passing gas through the reaction mixture, under vigorous stirring, while bubbling moisture-free N$_2$ gas through the reaction mixture at the reaction conditions given in TABLE-1 and measuring quantitatively the gaseous hydrogen halide evolved during the reaction by absorbing it in aqueous NaOH solution by a simple acid-base titration using phenolphthalein indicator, and then III) cooling the reaction mixture to room temperature (30° C.) and analyzing the products and unconverted reactants present in the reaction mixture, after separating the solid catalyst from it by filtration, by commonly used gas-liquid chromatographic technique using SE 30 column for chromatographic separation of reaction products, thermal conductivity detector and hydrogen as a carrier gas.

The results are included in TABLE-1.

TABLE 1

Reaction conditions and results of the alkylation of benzene and toluene o\ anionic clay hydrotalcite-type $[(Mg^{2+})_{0.75}(Ga^{3+})_{0.25}(OH)_2]^{0.25+}[CO_3^{2-}]_{0.125}\cdot qH_2O$ catalyst.

| Experiment No. | 1 | 2 | 3 | 4 | 5 |
|---|---|---|---|---|---|
| Reactants: | | | | | |
| Aromatic Compound (Ac) | $C_6H_6$ (benzene) | $C_6H_5CH_3$ (toluene) | $C_6H_5CH_3$ (toluene) | $C_6H_6$ (benzene) | $C_6H_6$ (benzene) |
| Alkylating agent (Aa) | $C_6H_5CH_2Cl$ | $C_6H_5CH_2Br$ | $C_6H_5CH_2Cl$ | $C_6H_5CH_2Cl$ | $4-NO_2C_6H_4CH_2Cl$ |
| Reaction Conditions: | | | | | |
| Solvent | nil | nil | nil | nil | nil |
| Ac/Aa mole ratio | 17 | 17 | 17 | 10 | 20 |
| Solvent/Aa mole ratio | 0.0 | 0.0 | 0.0 | 0.0 | 0.0 |
| Catalyst/Aa weight ratio | 0.2 | 0.1 | 0.1 | 0.04 | 0.2 |
| Temperature (° C.) | 80 | 110 | 50 | 80 | 105 |
| Pressure (atm) | 1.0 | 1.0 | 1.0 | 1.0 | 2.2 |
| GHSV of $N_2$ (h$^{-1}$) | 120 | 200 | 100 | 100 | 50 |
| Reaction time (h) | 0.1 | 0.05 | 2.0 | 0.5 | 1.0 |
| Conversion of alkylating agent (%) | above 99.9 | above 99.9 | above 99.9 | above 99.9 | above 99.9 |
| Main product of reaction | $C_6H_5CH_2C_6H_5$ (diphenyl methane) | $CH_3C_6H_4CH_2C_6H_5$ (benzyl toluene) | $CH_3C_6H_4CH_2C_6H_5$ (benzyl toluene) | $C_6H_5CH_2C_6H_5$ (diphenyl methane) | $4-NO_2C_6H_4CH_2C_6H_5$ (4-nitro benzyl benzene) |
| By-product of reaction | HCl | HBr | HCl | HCl | HCl |

Example-2

This example illustrates the repeated reuse of the catalyst prepared in Example 1, in the process of this invention for the alkylation of benzene and other aromatic hydrocarbons by benzyl chloride, benzyl bromide, benzyl alcohol or $C_6H_5C_4H_8Cl$, as an alkylating agent, to corresponding alkylated aromatic compounds.

The alkylation of benzene and other aromatic Hydrocarbons by benzyl chloride, benzyl bromide, benzyl alcohol or $C_6H_5C_4H_8Cl$, over the used and reused catalyst, prepared in Example 1, was carried out by the procedure same as that described in EXAMPLE-1, except the first step (i.e. the catalyst pre-treatment and washing step), at the reaction conditions given in TABLE-2. The results are included in TABLE-2. The catalyst used in Experiment No. 1 of Example 1 was reused repeatedly in the subsequent experiments (Experiment Nos. 6–10).

TABLE 2

Reaction conditions and results of the alkylation of different aromatic compounds over the repeatedly reused catalyst, prepared in Example 1.

| Experiment No. | 6 | 7 | 8 | 9 | 10 |
|---|---|---|---|---|---|
| Catalyst used: | that used in Expt. No. 1, after washing with toluene | that used in Expt. No. 6, after washing with benzene | that used in Expt. No. 7, after washing with toluene. | that used in Expt. No. 8, after washing with n-heptane | that used in E; No. 9, after washing with xylene |
| Reactants: | | | | | |
| Aromatic compound (Ac) | $C_6H_5CH_3$ (toluene) | $C_6H_6$ (benzene) | $C_6H_5CH_3$ (toluene) | $C_{14}H_{10}$ (anthracene) | p-$(CH_3)_2C_6H_4$ (p-xylene) |
| Alkylating agent (Aa) | $C_6H_5CH_2Cl$ | $C_6H_5C_4H_8Cl$ | $C_6H_5CH_2OH$ | $C_6H_5CH_2Cl$ | $C_6H_5CH_2Br$ |
| Reaction Conditions: | | | | | |
| Solvent | nil | nil | nil | n-heptane | nil |
| Ac/Aa mole ratio | 17 | 16 | 18 | 1.1 | 17 |
| Solvent/Aa mole ratio | 0.0 | 0.0 | 0.0 | 12 | 0.0 |
| Catalyst/Aa weight ratio- | 0.2 | 0.2 | 0.2 | 0.2 | 0.2 |
| Temperature (° C.) | 110 | 80 | 160 | 150 | 80 |
| Pressure (atm) | 1.0 | 1.0 | 3.0 | 5.0 | 1.0 |
| GHSV of $N_2$ ($h^{-1}$) | 120 | 150 | 250 | 300 | 120 |
| Reaction time (h) | 0.03 | 1.0 | 2.0 | 0.3 | 0.25 |
| Conversion of alkylating agent (%) | 99.5 | above 99.9 | above 99.9 | 99.6 | above 99.9 |
| Main product of reaction | $CH_3C_6H_4CH_2C_6H_5$ (benzyl toluene) | $C_6H_5C_4H_8C_6H_5$ (diphenyl butane) | $CH_3C_6H_4CH_2C_6H_5$ (benzyl toluene) | $C_{14}H_9CH_2C_6H_5$ (benzyl anthracene) | $(CH_3)_2C_6H_3CH_2C_6H_5$ (benzyl p-xylene) |
| By-product of reaction | HCl | HCl | $H_2O$ | HCl | HBr |

Example 3

This example illustrates the process of this invention for the alkylation of benzene, anisole and phenol by benzyl chloride in the presence or absence of any solvent, over $[(Zn^{2+})_{0.1}(Mg^{2+})_{0.8}(Ga^{3+})_{0.05}(In^{3+})_{0.05}(OH)_2]^{0.1+}$ $[CO_3^{2-}]_{0.05} \cdot qH_2O$ anionic clay catalyst.

The above catalyst was prepared as follows: First an aqueous solution containing 1.4 g (5.4 mmol) $Ga(NO_3)_3 \cdot xH_2O$, 2.1 g (5.4 mmol) $In(NO_3)_3 \cdot 5H_2O$, 2.0 g (10.7 mmol) $Zn(NO_3)_2 \cdot 6H_2O$ and 21.87 g (85.3 mmol) $Mg(NO_3)_2 \cdot 6H_2O$ in 100 cm³ of water prepared. 2.76 g (20 mmol) $K_2CO_3$ and 15.19 g (270.72 mmol) KOH in 300 cm³ of water were dissolved to make a second solution. These two solutions were added dropwise into a flask containing 200 cm³ of water at 313 K under vigorous stirring. The rate of addition of the two solutions was controlled in order to keep a constant pH of 11–12, which was monitored continuously throughout the coprecipitation, procedure by means of a pH-meter. After completing the addition of the solutions, the white gel obtained was immediately washed with deionized water several times and separated in a centrifuige. After this, the white paste was dried in an oven in static air at 353 K for 24 h.

The XRD data of the white solid anionic clay produced was obtained using CuKα radiations. The XRD data, 2θ value and relative intensity of major XRD peaks, of the anionic clay are given below:

| 2θ (degree): | 11.1 | 22.4 | 33.9 |
|---|---|---|---|
| Relative intensity (%): | 100 | 59 | 32 |

The XRD data are similar to that of hydrotalcite [ref Cavani et al. Catalysis Today, vol. 11, page 173–301, (1991)].

The alkylation reactions over the catalyst was carried out by the procedure same as that described in EXAMPLE-1 except that, in step I, the catalyst was pre-treated with HCl gas by bubbling dry HCl gas at a flow rate of 10 cm³min⁻¹ through a mixture of 0.5 g catalyst and 134 cm³ of n-heptane solvent in a stirred batch glass reactor at room temperature for 30 min and then washing the HCl treated catalyst with the liquid aromatic compound or solvent used in the reaction. The reaction conditions are given in TABLE-3. The results are included in TABLE-3.

TABLE 3

Reaction conditions and results of the alkylation of different aromatic compounds over the anionic clay
$[(Zn^{2+})_{0.1}(Mg^{2+})_{0.8}(Ga^{3+})_{0.05}(In^{3+})_{0.05}(OH)_2]^{0.1+}[CO_3^{2-}]_{0.05} \cdot qH_2O$ catalyst.

| Experiment No. | 11 | 12 | 13 |
|---|---|---|---|
| Reactants: | | | |
| Aromatic compound (Ac) | $C_6H_6$ (benzene) | $CH_3OC_6H_5$ (anisole) | $C_6H_5OH$ (phenol) |
| Alkylating agent (Aa) | $C_6H_5CH_2Cl$ | $C_6H_5CH_2Cl$ | $C_6H_5CH_2Cl$ |
| Reaction Conditions: | | | |
| Solvent | Nil | Nil | n-octane |
| Ac/Aa mole ratio | 17.0 | 17.0 | 1.0 |
| Solvent/Aa mole ratio | 0.0 | 0.0 | 9.4 |
| Catalyst/Aa weight ratio | 0.5 | 0.5 | 0.5 |
| Temperature (° C.) | 80 | 80 | 80 |
| Pressure (atm) | 1.0 | 1.0 | 1.0 |
| GHSV of $N_2$ ($h^{-1}$) | 100 | 100 | 100 |
| Reaction time (h) | 0.2 | 0.1 | 0.1 |
| Conversion of aralkylating agent (%) | above 99.9 | above 99.9 | above 99.9 |
| Main product of reaction | $C_6H_5CH_2C_6H_5$ (diphenyl methane) | $CH_3OC_6H_4CH_2C_6H_5$ (benzyl anisole) | $HOC_6H_4CH_2C_6H_5$ (benzyl phenol) |
| By-product of reaction | HCl | HCl | HCl |

Example-4

This example illustrates the process of this invention for the acylation of benzene, toluene, sole and 2-naphthol by benzoyl chloride or acetyl chloride, using theicatalyst prepared in Example 1.

The acylation reaction over the catalyst was carried out by the procedure same as that described EXAMPLE-1 except that, in step I, the catalyst is pre-treated by passing dry HCl gas at a flow rate of $cm^3 \cdot min^{-1}$ over the 0.4 g catalyst kept in a glass reactor at room temperature (28° C.) for 1 h. The reaction conditions are given in TABLE-4. The results are included in TABLE-4.

TABLE 4

Reaction conditions and results of the acylation of benzene, toluene, anisole and 2-naphthol over the catalyst prepared in Example 1.

| Experiment No. | 14 | 15 | 16 | 17 |
|---|---|---|---|---|
| Reactants: | | | | |
| Aromatic Compound (Ac) | $C_6H_6$ (benzene) | $CH_3C_6H_5$ (toluene) | $CH_3OC_6H_5$ (anisole) | $2\text{-}HOC_{10}H_7$ (2-naphthol) |
| Acylating agent (Aa) | $C_6H_5COCl$ | $C_6H_5COCl$ | $C_6H_5COBr$ | $CH_3COCl$ |
| Reaction Conditions | | | | |
| Solvent | Nil | Nil | Nil | dichloroethane |
| Ac/Aa mole ratio | 17.0 | 17.0 | 17.0 | 1.1 |
| Solvent/Aa mole ratio | 0.0 | 0.0 | 0.0 | 20 |
| Catalyst/Aa weight ratio | 0.4 | 0.4 | 0.4 | 0.4 |
| Temperature (° C.) | 80 | 110 | 140 | 60 |
| Pressure (atm) | 1.0 | 1.0 | 1.0 | 1.3 |
| GHSV of $N_2$ ($h^{-1}$) | 120 | 120 | 120 | 120 |
| Reaction time (h) | 3.0 | 0.5 | 0.3 | 0.2 |
| Conversion of acylating agent (%) | 90.7 | 99.8 | 99.9 | Above 99.9 |
| Main product of reaction | $C_6H_5COC_6H_5$ (benzophenone) | $CH_3C_6H_4COC_6H_5$ (benzoyl toluene) | $CH_3OC_6H_4COC_6H_5$ (benzoyl anisole) | $2\text{-}HOC_{10}H_6COCH_3$ (acetyl-2-naphthol) |
| By-product of reaction | HCl | HCl | HBr | HCl |

Example-5

This example illustrates the process of this invention for the alkylation or acylation of benzene and other aromatic compounds by benzyl chloride or benzoyl chloride to corresponding alkylated or acylated aromatic compounds, using a $[(Mg^{2+})_{0.7}(In^{3+})_{0.3}(OH)_2]^{0.3+}[CO_3^{2-}]_{0.15}.qH_2O$ anionic clay catalyst.

The above anionic clay catalyst was prepared as follows: First an aqueous solution containing 12.5 g (31.98 mmol) $In(NO_3)_3.5H_2O$ and 19:13 g (74.62 mmol) $Mg(NO_3)2.6 H_2O$ in 100 cm$^3$ of water was prepared. 2.76 g (20 mmol) $K_2CrO_3$ and 15.19 g (270.72 mmol) KOH in 300 cm$^3$ of water were dissolved to make a second solution. These two solutions were added dropwise into a flask containing 200 cm$^3$ of water at 313 K under vigorous stirring. The rate of addition of the two solutions was controlled in order to keep a constant pH of 11–12, which was monitored continuously throughout the coprecipitation procedure by means of a pH-meter. After completing the addition of the solutions, the white gel obtained was immediately washed with deionised water several times and separated in a centrifuge. After this, the white paste was dried in an oven in static air at 353 K for 24 h.

The XRD data of the white solid anionic clay produced was obtained using CuKα radiations. The XRD data, 2θ value and relative intensity of major XRD peaks, of the anionic clay are given below:

| 2θ (degree): | 11.2 | 22.4 | 33.8 |
|---|---|---|---|
| Relative intensity (%): | 100 | 61 | 33 |

The XRD data are similar to that of hydrotalcite [ref Cavani et al. Catalysis Today, vol. 11, page 173–301, (1991)].

The alkylation or acylation of benzene and other aromatic compounds over the catalyst was carried out by the procedure same as that described in EXAMPLE-1 except that, instead of benzyl chloride, benzoyl chloride was used for pretreating the catalyst in step I and the pretreated catalyst, after its first used in Experiment No.18, was repeatedly reused in the subsequent experiements (Experiment Nos. 19–21). The reaction conditions are given in TABLE-5. The results are presented in TABLE-5.

TABLE 5

Reaction conditions and results of the alkylation or acylation of benzene, toluene, mesitylene and phenol.

| Experiment No. | 18 | 19 | 20 | 21 |
|---|---|---|---|---|
| Reactants: | | | | |
| Aromatic Compound (Ac) | $C_6H_6$ (benzene) | $CH_3C_6H_5$ (toluene) | $(CH_3)_3C_6H_3$ (mesitylene) | $HOC_6H_5$ (phenol) |
| Alkylating or Acylating agent (Aa) | $C_6H_5CH_2Cl$ | $C_6H_5COCl$ | $C_6H_5COCl$ | $C_6H_5COCl$ |
| Reaction Conditions | | | | |
| Solvent | nil | nil | nil | dichloroethane |
| Ac/Aa mole ratio | 17.0 | 17.0 | 17.0 | 1.0 |
| Solvent/Aa mole ratio | 0.0 | 0.0 | 0.0 | 10.0 |
| Catalyst/Aa weight ratio | 0.4 | 0.4 | 0.4 | 0.4 |
| Temperature (° C.) | 80 | 110 | 162 | 60 |
| Pressure (atm) | 1.0 | 1.0 | 1.0 | 1.0 |
| GHSV of $N_2$ (h$^{-1}$) | 100 | 150 | 200 | 100 |
| Reaction time (h) | 0.1 | 0.6 | 0.3 | 1.0 |
| Conversion of acylating agent (%) | 99.8 | 98.9 | 99.5 | >99.9 |
| Main product of reaction | $C_6H_5CH_2C_6H_5$ (diphenyl methane) | $CH_3C_6H_4COC_6H_5$ (benzoyl toluene) | $(CH_3)_3C_6H_2COC_6H_5$ (benzoyl mesitylene) | $HOC_6H_4COC_6H_5$ (benzoyl phenol) |
| By-product of reaction | HCl | HCl | HBr | HCl |

Example-6

This comparative example illustrates the process of this invention for the alkylation or acylation of toluene by benzyl chloride or benzoyl chloride, using the catalysts prepared in Examples 1, 3 and 5 without their pre-treatment in step I of the process of this invention.

The alkylation or acylation reaction was carried out over the catalysts prepared in Examples 1, 3 and 5, by the procedure same as that described in EXAMPLE-1, except that the catalysts were not pre-treated with any halo compound in step I. The reaction conditions are given in TABLE-6. The results are included in TABLE-6.

The results in TABLE-6 clearly show that all the three catalysts show extremely poor activity in the process of this invention for the alkylation or acylation reaction, when the catalysts are not pre-treated by the step I of the process of this invention. All the three catalysts, when pre-treated by halo compound in step I of the process of this invention, show very high activity, i.e. very high conversion of the alkylating or acylating agent, in all the experiments (Experiment Nos. 1–21).

TABLE 6

Reaction conditions and results of the alkylation or acylation of toluene over the catalysts, prepared in Examples 1, 3 and 5, without pretreatment by halo-compounds in step I of the process of this invention.

| Experiment No. | 22 | 23 | 24 | 25 |
|---|---|---|---|---|
| Catalyst | Prepared in Example 1 | Prepared in Example 3 | Prepared in Example 5 | Prepared in Example 1 |
| Reactants: | | | | |
| Aromatic Compound (Ac) | $CH_3C_6H_5$ (toluene) | $CH_3C_6H_5$ (toluene) | $CH_3C_6H_5$ (toluene) | $CH_3C_6H_5$ (toluene) |
| Alkylating or Acylating agent (Aa) | $C_6H_5CH_2Cl$ | $C_6H_5COCl$ | $C_6H_5CH_2Cl$ | $C_6H_5COCl$ |
| Reaction Conditions | | | | |
| Solvent | Nil | Nil | Nil | Nil |
| Ac/Aa mole ratio | 17.0 | 17.0 | 17.0 | 17.0 |
| Solvent/Aa mole ratio | 0.0 | 0.0 | 0.0 | 0.0 |
| Catalyst/Aa weight ratio | 0.1 | 0.4 | 0.1 | 0.4 |
| Temperature (° C.) | 110 | 110 | 110 | 110 |
| Pressure (atm) | 1.0 | 1.0 | 1.0 | 1.0 |
| GHSV of $N_2$ ($h^{-1}$) | 120 | 120 | 120 | 120 |
| Reaction time (h) | 1.0 | 3.0 | 1.0 | 3.0 |
| Conversion of alkylating or acylating agent (%) | 5 | 3 | 6 | 5 |
| Main product of reaction | $CH_3C_6H_4CH_2C_6H_5$ (benzyl toluene) | $CH_3C_6H_4COC_6H_5$ (benzoyl toluene) | $CH_3C_6H_4CH_2C_6H_5$ (benzyl toluene) | $CH_3C_6H_4COC_6H_5$ (benzoyl toluene) |
| By-product of reaction | HCl | HCl | HBr | HCl |

Example-7

This comparative example illustrates the process of this invention for the alkylation or acylation of benzene by benzyl chloride or benzoyl chloride using the catalyst prepared in Example 1, even when an appreciable amount of moisture is present in the reaction mixture.

The alkylation or acylation of benzene over the catalyst prepared in Example 1 was carried out by the procedure same as that described in EXAMPLE-1, except that in the present case the reaction was carried out using dry (moisture-free benzene) or wet benzene (benzene saturated with water at 30° C.). The reaction conditions are given in TABLE-7.

The results in TABLE-7 show that the catalyst of this invention catalyses the alkylation or acylation reaction even when moisture is present in the reaction mixture.

TABLE 7

Reaction conditions and results of the alkylation or acylation of benzene with or without containing moisture.

| Experiment No. | 26 | 27 | 28 | 29 |
|---|---|---|---|---|
| Reactants: | | | | |
| Aromatic Compound (Ac) | Dry benzene | Benzene saturated with water at 30° C. | Dry benzene | Benzene saturated with water at 30° C. |
| Alkylating or Acylating agent (Aa) | $C_6H_5CH_2Cl$ | $C_6H_5CH_2Cl$ | $C_6H_5COCl$ | $C_6H_5COCl$ |
| Reaction Conditions | | | | |
| Solvent | Nil | Nil | Nil | Nil |
| Ac/Aa mole ratio | 17.0 | 17.0 | 17.0 | 17.0 |
| Solvent/Aa mole ratio | 0.0 | 0.0 | 0.0 | 0.0 |
| Catalyst/Aa weight ratio | 0.1 | 0.1 | 0.5 | 0.5 |
| Temperature (° C.) | 80 | 80 | 80 | 80 |
| Pressure (atm) | 1.0 | 1.0 | 1.0 | 1.0 |
| GHSV of $N_2$ ($h^{-1}$) | 150 | 150 | 150 | 150 |

TABLE 7-continued

Reaction conditions and results of the alkylation or acylation of benzene with or without containing moisture.

| Experiment No. | 26 | 27 | 28 | 29 |
|---|---|---|---|---|
| Reaction time (h) | 0.3 | 0.3 | 5.0 | 5.0 |
| Conversion of alkylating or acylating agent (%) | above 99.9 | above 99.9 | 99.5 | 99.7 |
| Main product of reaction | $C_6H_5CH_2C_6H_5$ (diphenyl methane) | $C_6H_5CH_2C_6H_5$ (diphenyl methane) | $C_6H_5COC_6H_5$ (benzophenone) | $C_6H_5COC_6H_5$ (benzophenone) |
| By-product of reaction | HCl | HCl | HCl | HCl |

The main advantages of the process of this invention over the prior art processes for the alkylation or acylation of aromatic compound are as follows:

1) The process of this invention has a number of advantages over the earlier homogeneous acid catalyzed processes for the alkylation or acylation of aromatic compounds, as follows:

In the process of this invention,
  i) the catalyst used is heterogeneous solid catalyst and hence it can be separated from the reaction products simply by filtration,
  ii) the separated catalysts can be reused in the process to a number of times, and
  iii) also the catalyst is non corrosive, therefore most of the serious problems associated with homogeneous catalyst used in the earlier homogeneous catalyzed processes for the preparation of alkylated or acylated aromatic compounds are overcome in the process of this invention.

2) The process of this invention has also number of advantages over the prior art processes based on the use of solid acid catalyst for the alkylation or acylation of aromatic compounds, as follows:
  i) The activity of the said catalyst used in the process of present invention is very high and hence the reaction is very fist and thereby the time required for completing the reaction is very short.
  ii) The catalyst of this invention can be reused repeatedly in the process and the reused catalyst shows very high activity in the process even after its repeated use for a number of times in the process.
  iii) The process of the present invention can be used for alkylating or acylating both small and large size aromatic compounds with both small and large size alkylating or acylating agents to produce the corresponding alkylated or acylated aromatic compounds.
  iv) In the process of this invention, when inert gas is bubbled through the reaction mixture continuously, said by-product formed in the reaction is removed continuously, and thereby the reverse alkylation or acylation reaction is avoided or minimized, thus requiring short time for completing the reaction.
  v) In the process of this invention, by using pressure higher than 1 atm, it is possible to carry out the alkylation or acylation reaction at a temperature higher than the normal boiling point of either of the reactants and the solvent, and thereby the reaction period for completing the reaction is shortened and/or the inhibition of the reaction due to strong adsorption of the reactants, products or solvent on the catalyst is avoided or minimized.
  vi) By the process of this invention, even the alkylation or acylation of benzene, which does not contain any aromatic ring activating electron donating group such as alkyl, alkoxy, hydroxy etc. group, is rapid at mild reaction conditions and hence the reaction is accomplished at a short reaction period.
  vii) In the process of this invention, by using the basic solid anionic clay hydrotalcite-type catalyst, a rapid alkylation or acylation of aromatic compound is possible even when the reaction mixture contains moisture; the catalyst is not deactivated due to the presence of moisture in the reaction mixture. Hence, unlike the prior art homogeneous and solid acid catalysts, the catalyst of this invention does not demand moisture-free conditions to be active in the process and hence there is no need to remove traces of moisture from the catalyst, reactants or solvent used in the process, and thereby the process of this invention becomes more economical.
  viii) Since the catalyst use in the process of this invention is basic in nature, this process can be used for alkylating or acylating even acid sensitive aromatic compounds or basic aromatic compounds.

What is claimed is:

1. A process for Friedel-Crafts liquid phase alkylation of an aromatic compound using a basic anionic clay hydrotalcite solid catalyst, said compound is represented by a formula:

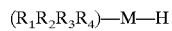

$(R_1R_2R_3R_4)—M—H$ which being reacted with an alkylating agent represented by a formula:

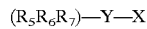

$(R_5R_6R_7)—Y—X$ to produce corresponding alkylated aromatic compound represented by a formula:

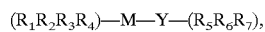

$(R_1R_2R_3R_4)—M—Y—(R_5R_6R_7),$ wherein M is an aromatic nucleus; $R_1$, $R_2$, $R_3$ and $R_4$ are groups attached to the aromatic nucleus, M; Y, which is a nucleus of alkylating agent, is selected from $C_6H_2—C_nH_{2n}$, $C_6H_2—CO$, $C_nH_{2n-2}$, $C_mH_{2m-4}$ and $C—CO$; $R_5$, $R_6$ and $R_7$ are groups attached to the nucleus of alkylating agent, Y; X is a halogen or hydroxyl chemical group; H is hydrogen; C is carbon; O is oxygen; n and m are integer numbers having value above zero and above one, respectively; using a basic anionic clay catalyst represented by a formula:

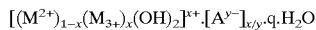

where $M^{2+}$ is a divalent cation selected from $Mg^{2+}$, $Zn^{2+}$ $Ni^{2+}$, $Co^{2+}$, $Mn^{2+}$, $Cu^{2+}$ or a mixture thereof; $M^{3+}$ is a trivalent cation selected from $Ga^{3+}$, $In^{3+}$ $Al^{3+}$ $Fe^{3+}$ $Cr^{3+}$ or a mixture thereof; x is a mole fraction of trivalent cations in the range of about 0.05 to about 0.5; O is oxygen; H is hydrogen; $A^{y-}$ is an anion; y minus is an anionic negative charge having a value of 1 minus or 2 minus; and q is a number of water molecules, as the water of hydration; and said catalyst having X-ray diffraction pattern similar to that of a typical hydrotalcite anionic clay material, with or without supporting it on a porous catalyst carrier;

the said process comprises:

i. pretreating said catalyst by contacting it with a halogen containing compound in the presence or absence of a non-aqueous solvent and optionally washing the pretreated catalyst with non-aqueous solvent or liquid aromatic compound to be alkylated, and then ii. contacting a liquid reaction mixture comprising said aromatic compound and said alkylating agent in the presence or absence of a non-aqueous solvent with the catalyst obtained from step (i) in a stirred batch reactor fitted with a reflux condenser under vigorous stirring, in the presence or absence of an inert gas bubbling through the reaction mixture, at following reaction conditions: weight ratio of catalyst to alkylating agent in the range from about 0.01 to about 2.0, mole ratio of aromatic compound to alkylating agent in the range from about 0.1 to about 100, weight ratio of non-aqueous solvent to aromatic compound in the range from zero to about 100, reaction temperature in the range from about 10° C. to about 300° C., pressure in the range from about 0.5 aim to about 10 atm, gas hourly space velocity of inert gas bubbled through the liquid reaction mixture in the iii. range from zero $h^{-1}$ to about 5000 $h^{-1}$ and reaction period in the range from about 0.02 h to about 100 h;

iii. cooling the reaction mixture to a temperature about 30° C., removing said catalyst from the reaction mixture by filtration and then separating the reaction products from the reaction mixture, and optionally washing the used catalyst by non-aqueous solvent; and optionally, iv. reusing the used catalyst directly with or without drying for the subsequent reaction batch avoiding step (i).

2. A process as claimed in claim 1, wherein the reaction is carried out by alkylation of aromatic compounds using a reusable basic anionic clay catalyst.

3. A process as claimed in claim 1, wherein each of the $R_1$, $R_2$, $R_3$ and $R_4$ chemical groups is selected from hydrogen, alkane, olefinic, phenyl, alkoxy, phenoxy, hydroxyl, aldehydic, ketonic, amine, amide, cyano, halo, nitro, mercapto, alkyl mercapto, thio and sulphonic acid groups.

4. A process as claimed in claim 1, wherein X is Cl, Br or OH.

5. A process as claimed in claim 1, wherein each of the $R_5$, $R_6$ and $R_7$ chemical groups is selected from hydrogen, alkane, olefinic, phenyl, halogen, nitro, alkoxy, phenoxy and cyano groups.

6. A process as claimed in claim 1, wherein the divalent cation, $M^{2+}$, of said catalyst is $Mg^{2+}$, $Zn^{2+}$ or a mixture thereof.

7. A process as claimed in claim 1, wherein the trivalent cation, $M^{3+}$, of said catalyst is $Ga^{3+}$, $In^{3+}$ $Fe^{3+}$ or a mixture there of.

8. A process as claimed in claim 1, wherein the mole fraction, x, of the trivalent cation of said catalyst is in the range from about 0.1 to about 0.4.

9. A process as claimed in claim 1, wherein the anion, $A^{y-}$, of said catalyst is $CO_3^{2-}$, $OH^1$, $(CH_3COO)^{1-}$, $(SO4)^{2-}$, $(HSO_4)^{-1}$, $(HCO_3)^{1-}$, $(NO_3)^{1-}$, $(ClO_4)^{1-}$, a mixture thereof.

10. A process as claimed in claim 1, wherein the halogen containing compound used for pre treating said catalyst in step I is selected from gaseous HCl, HBr, $Cl_2$ and $Br_2$ or from liquid organic halo compounds.

11. A process as claimed in claim 1, wherein the weight ratio of catalyst to alkylating agent is in the range from about 0.03 to about 0.9.

12. A process as claimed in claim 1, wherein the mole ratio of aromatic compound to alkylating agent is in the range from about 1.0 to about 20.

13. A process as claimed in claim 1, wherein the weight ratio of non-aqueous solvent to aromatic compound is in the range from zero to about 20.

14. A process as claimed in claim 1, wherein the reaction temperature is in the range from about 20° C. to about 200° C.

15. A process as claimed in claim 1, wherein the reaction pressure is in the range from about 1 atm to about 5 atm.

16. A process as claimed in claim 1, wherein the reaction period is in the range from about 0.05 h to about 20 h.

17. A process as claimed in claims 1, wherein the space velocity of inert gas in the range from about 50 $h^{-1}$ to about 500 $h^{-1}$.

18. A process as claimed in claim 1, wherein when the reaction employs a solvent, the solvent is selected from the group consisting of ethylene dichloride, nitrobenzene, nitromethane, chlorobenzene, n-hexane, n-heptane, n-octane, and combinations thereof.

* * * * *